(12) United States Patent
Long et al.

(10) Patent No.: US 11,110,075 B2
(45) Date of Patent: Sep. 7, 2021

(54) USE OF DAPHNETIN IN IMPROVING FUNCTION OF AORTIC ENDOTHELIAL CELL

(71) Applicant: XI'AN JIAOTONG UNIVERSITY, Xi'an (CN)

(72) Inventors: Jian-Gang Long, Xi'an (CN); Xu-Yun Liu, Xi'an (CN); Jian-Kang Liu, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 134 days.

(21) Appl. No.: 16/659,477

(22) Filed: Oct. 21, 2019

(65) Prior Publication Data

US 2021/0046043 A1    Feb. 18, 2021

(30) Foreign Application Priority Data

Aug. 14, 2019    (CN) .......................... 201910746863.6

(51) Int. Cl.
| | | |
|---|---|---|
| *A61K 31/353* | (2006.01) | |
| *A23L 33/10* | (2016.01) | |
| *A61P 9/10* | (2006.01) | |
| *A61P 9/00* | (2006.01) | |

(52) U.S. Cl.
CPC ............ *A61K 31/353* (2013.01); *A23L 33/10* (2016.08); *A61P 9/00* (2018.01); *A61P 9/10* (2018.01); *A23V 2002/00* (2013.01)

(58) Field of Classification Search
CPC ....... A61K 31/353; A61K 31/37; A23L 33/10; A61P 9/10; A61P 9/00; A23V 2002/00
USPC .......................................................... 514/457
See application file for complete search history.

(56) References Cited

FOREIGN PATENT DOCUMENTS

| CN | 1872053 | * | 12/2006 |
| CN | 106377559 | * | 2/2017 |
| WO | WO2017146341 | * | 8/2017 |

* cited by examiner

*Primary Examiner* — Taylor V Oh

(57) ABSTRACT

The disclosure relates to a pharmaceutical composition including daphnetin, a method for improving aortic endothelial cell function, and use of daphnetin in preparation of a medicine for improving aortic endothelial cell function. The daphnetin is capable of inhibiting inflammatory response of the human aortic endothelial cells caused by a saturated fatty acid, and preventing an occurrence and progression of atherosclerosis. The daphnetin is capable of reducing human aortic endothelial inflammation caused by a saturated fatty acid, for example, reducing the mRNA levels of interleukin-6 (IL-6), and is capable of effectively protecting the function of mitochondria in human aortic endothelium from being damaged by a saturated fatty acid.

5 Claims, 2 Drawing Sheets

Specification includes a Sequence Listing.

USE OF DAPHNETIN IN IMPROVING FUNCTION OF AORTIC ENDOTHELIAL CELL

SEQUENCE LISTING

This application contains a Sequence Listing in computer readable form. The computer readable form is incorporated herein by reference.

CROSS-REFERENCE TO RELATED APPLICATION

This application claims all benefits accruing under 35 U.S.C. § 119 from China Patent Application No. 201910746863.6, filed on Aug. 14, 2019 in the China National Intellectual Property Administration, the content of which is hereby incorporated by reference.

FIELD

The present disclosure belongs to the pharmaceutical field, and particularly relates to a pharmaceutical composition including daphnetin, a method for improving aortic endothelial cell function, and use of daphnetin in preparation of a medicament for improving aortic endothelial cell function.

BACKGROUND

Statistical data released by World Health Organization (WHO) in 2011 shows that deaths caused by cardiovascular diseases account for 31% of global deaths, second only to the total of other non-communicable diseases. It is expected that the mortality caused by cardiovascular diseases will be significantly higher than other diseases from 2008 to 2030, taking the lead position. The pathological basis of cardiovascular diseases and cerebrovascular diseases, such as myocardial infarction and cerebral infarction, is atherosclerosis.

Atherosclerosis, whose pathogenesis is very complex, is a chronic inflammatory response with plaques inside arteries, and accompanied by damages to vascular endothelial cells. The main factors leading to atherosclerosis are an unhealthy diet such as high-salt, high-fat, and high-energy diet, smoking, and metabolic risk factors, including diseases such as "Three-High" symptom (hypertension, hyperglycemia, and hyperlipidemia) and obesity.

Although atherosclerosis may be treated by medicine or surgery, it is latent leading to a high lethality rate and a high disability rate. Therefore, prevention and early treatment of atherosclerosis are particularly favorable. Studies have revealed that natural active ingredients such as chlorogenic acid, "Xiongshao" (Ligusticum chuanxiong and Paeoniae rubra radix) and lignans have anti-atherosclerotic effects, and functional foods containing these ingredients are available on the market. It is of great significance and prospect to explore natural substances that are effective against cardiovascular diseases such as atherosclerosis.

SUMMARY

The present disclosure provides a pharmaceutical composition containing daphnetin, a method for improving aortic endothelial cell function, and use of daphnetin in preparation of a medicament for improving aortic endothelial cell function.

Daphnetin is found to be capable of significantly inhibiting inflammatory response of human aortic endothelial cells induced by a saturated fatty acid, and increase a production of mitochondrial membrane fusion related protein mitofusin 1 (Mfn1) in vascular endothelial cells, preventing the occurrence and development of atherosclerosis by anti-inflammatory and protecting mitochondrial function.

Daphnetin is capable of promoting viability of human aortic endothelial cells inhibited by a saturated fatty acid, and has an inhibitory effect on an inflammation of aortic endothelial cells caused by a saturated fatty acid.

Daphnetin is capable of reducing a mRNA level corresponding to interleukin-6 (IL-6) in aortic endothelial cells.

Daphnetin is capable of protecting mitochondria from being damaged by inflammation of aortic endothelial cells caused by a saturated fatty acid.

Daphnetin is capable of increasing an expression of mitochondrial membrane fusion related protein Mfn1 in vascular endothelial cells.

The present disclosure provides the pharmaceutical composition that includes daphnetin.

The pharmaceutical composition can be medicine or nutritional supplement that includes daphnetin.

The pharmaceutical composition can further include a pharmaceutical acceptable diluent, an excipient, and/or a carrier.

The present disclosure provides a method for improving function of an aortic endothelial cell, the method includes contacting the cell with an effective amount of daphnetin.

The present disclosure provides a method for inhibiting saturated fatty acid induced inflammation of an aortic endothelial cell, the method includes contacting the cell with an effective amount of daphnetin.

The present disclosure provides a method for reducing a mRNA level corresponding to interleukin-6 (IL-6) in an aortic endothelial cell, the method includes contacting the cell with an effective amount of daphnetin.

The present disclosure provides a method for protecting a mitochondrion from being damaged by saturated fatty acid induced inflammation of an aortic endothelial cell, the method includes contacting the cell with an effective amount of daphnetin.

The present disclosure provides a method for increasing an expression of mitochondrial membrane fusion related protein Mfn1 in an aortic endothelial cell, the method includes contacting the cell with an effective amount of daphnetin.

The present disclosure provides a method for preventing or treating a cardiovascular disease, the method includes administering to a patient in need thereof a therapeutically effective amount of daphnetin or the pharmaceutical composition.

The present disclosure provides a method for preventing atherosclerosis, the method includes administering to a patient in need thereof a therapeutically effective amount of daphnetin or the pharmaceutical composition.

The present disclosure provides use of daphnetin in preparing the pharmaceutical composition for improving aortic endothelial cell function.

The present disclosure provides use of daphnetin in preparing the pharmaceutical composition for preventing or treating a cardiovascular disease.

The present disclosure provides use of daphnetin in preparing the pharmaceutical composition for preventing atherosclerosis.

The present disclosure provides use of daphnetin in preparing a medicine or nutritional supplement for preventing or treating atherosclerosis.

Daphnetin has a protecting effect for growth of human aortic endothelial cells inhibited by saturated fatty acids. Daphnetin is found to be capable of significantly promoting viability of human aortic endothelial cells inhibited by saturated fatty acids, inhibiting the inflammatory response of human aortic endothelial cells induced by saturated fatty acids, and increasing the production of a mitochondrial membrane fusion related protein Mfn1 in vascular endothelial cells, in vascular diseases such as atherosclerosis that has a damage or inflammatory response on vascular endothelium. The daphnetin prevents the occurrence and development of atherosclerosis by anti-inflammation and protecting the mitochondria.

Daphnetin is capable of promoting the growth of human aortic endothelial cells inhibited by saturated fatty acids, effectively reducing inflammation of human aortic endothelial cells caused by saturated fatty acids, for example, reducing a level of mRNAs corresponding to interleukin-6 (IL-6). Daphnetin is capable of effectively protecting the function of the mitochondria in human aortic endothelial cells from being damaged by saturated fatty acids, for example, increasing an expression of mitochondrial membrane fusion related protein Mfn1. Use of daphnetin in the pharmaceutical composition, the medicine, and the nutritional supplement has a good application prospect in preventing the occurrence and development of vascular diseases.

BRIEF DESCRIPTION OF THE DRAWINGS

Implementations are described by way of example only with reference to the attached figures.

FIG. 3A and FIG. 3B are diagrams showing that daphnetin is capable of avoiding a palmitic acid-induced decrease of mitochondrial membrane fusion related protein Mfn1 expression in human aortic endothelial cells, wherein FIG. 3A shows a Western blot testing result, FIG. 3B is a statistical diagram based on the Western blot testing result, the abscissa of FIG. 3B represents the protein name, and the ordinate of FIG. 3B represents relative protein expression level.

DETAILED DESCRIPTION

Figure 1:
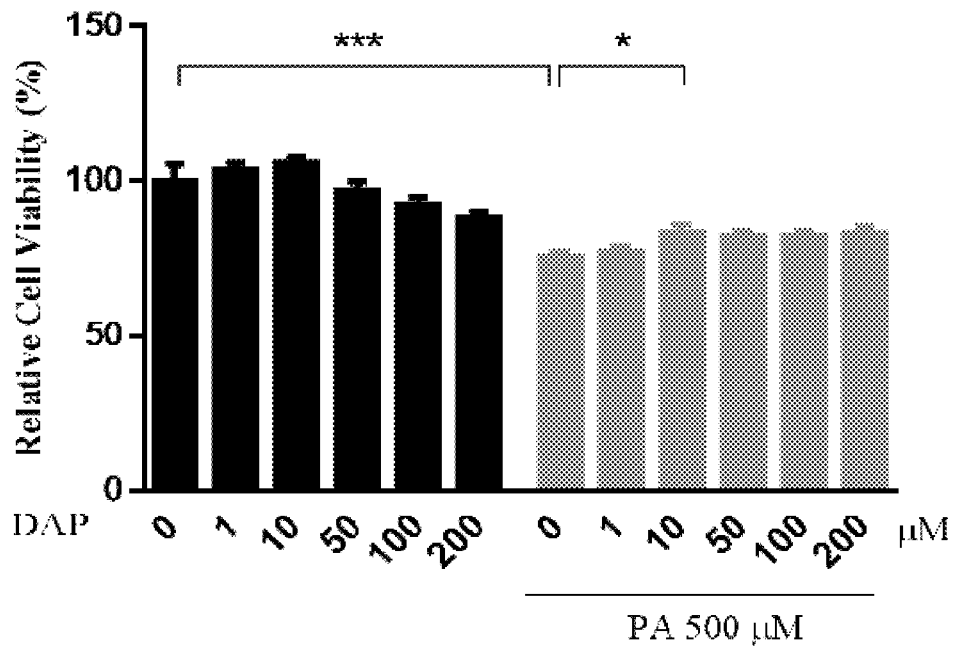
FIG. 1 is a diagram showing effects of daphnetin in different concentrations on cell viability of human aortic endothelial cells, wherein the abscissa represents the concentration of daphnetin (DAP), and the ordinate represents relative cell viability.

A detailed description with the above drawings is made to further illustrate the present disclosure.

Daphnetin (DAP), 7,8-dihydroxycoumarin, is an active ingredient extracted from Daphne Korean Nakai, and is a representative monomer of coumarins. Daphnetin has anti-inflammatory, anti-oxidation, anti-diabetes and liver-protecting effects, can be clinically used in adjuvant therapy for thromboangiitis obliterans, and other occlusive vascular diseases and coronary heart disease.

1. Experimental Materials

Daphnetin was purchased from Nanjing Puyi Biotechnology Co., Ltd. Daphnetin solutions with different concentrations, 0 μmol/L (μM), 1 μM, 10 μM, 50 μM, 100 μM, and 200 μM, were prepared by dissolving daphnetin in water.

TRIzol™ reagent was purchased from Invitrogen™. RNA reverse transcription kit and SYBR fluorescent dye were purchased from Takara Biotechnology (Dalian) Co., Ltd. RNA primers were ordered from and synthesized by Xi'an Qingkezexi Bio Co., Ltd.

2. Culture of Experimental Cells and Model Establishment

Human aortic endothelial cells (HAECs) were purchased from Shanghai Bioleaf Biotech Co., Ltd. Palmitic acid (PA) was purchased from SIGMA Company. A palmitic acid solution having a concentration of 500 μM was prepared by dissolving palmitic acid in water. A cell culture incubator was adopted to culture the cells in a temperature-constant, humidified, sterile condition. The cells were cultured in wells of culture plates at an atmosphere of 95% air and 5% $CO_2$ at 37° C. in the incubator. The experiments were performed on different experimental groups of cells.

3. Experimental Methods (1) MTT (3-(4,5-Dimethylthiazol-2-yl)-2,5-diphenyltetrazolium Bromide) Assay The HAECs that were previously cultured in a 12-well cell culture plates were divided into 6 different experimental groups and respectively applied with daphnetin in different concentrations, 0 μM, 1 μM, 10 μM, 50 μM, 100 μM, and 200 μM, all followed with an 24-hour incubation. Then, each of the 6 groups of cells was further divided into two subgroups; one was applied with 500 μM palmitic acid, the other was not, and all followed with another 24-hour incubation.

An MTT assay was performed to all groups of cells. The MTT assay was a laboratory test and standard colorimetric assay for measuring the activity of enzymes that reduced MTT to formazan, giving a purple color. Yellow MTT was reduced to purple formazan in living cells. For each group, HAECs were washed with phosphate-buffered saline (PBS) once, applied with 0.5 mg/ml of MTT, and cultured in the incubator containing 95% air and 5% $CO_2$ at 37° C. for 4 hours. The cultured cells were then washed three times with PBS before adding dimethyl sulfoxide (DMSO) to turn the insoluble purple formazan product into a colored solution. The absorbance was measured at a wavelength of 490 nm in a spectrophotometer. The absorbance of this colored solution can be quantified by measuring at a certain wavelength (usually between 500 and 600 nm) by a spectrophotometer.

(2) IL-6 mRNA Level Detection

The HAECs that were previously cultured in a 12-well cell culture plate were divided into 4 different experimental groups and respectively applied with daphnetin in the respective concentrations, 0 μM, 0 μM, 50 μM, 100 μM, and all followed with an 24-hour incubation. Then, the last 3 groups of cells were respectively applied with 500 μM palmitic acid, the first was not, and all followed with another 24-hour incubation. The detecting of mRNA levels corresponding to interleukin-6 (IL-6) was respectively carried out on each group of cells by using reverse transcription RNA and real-time quantitative polymerase chain reaction (PCR), and the specific method is as follows:

1) RNA Extraction

The medium for cell culture in the wells was removed. 500 μL of TRIzol™ reagent was added to each well, and the culture plate was then shaken at room temperature for 5 minutes. Then the cells in the wells were collected and transferred to a 1.5 mL eppendorf (EP) tube. 200 µl (taking ⅕ of total volume of the substance in the EP tube) of chloroform was then added to the EP tube for extraction of protein. The samples were then vigorously stirred for 15 seconds, rested for 15 minutes at room temperature, and then centrifuged at a relative centrifugal force of 12,000 g for 10 minutes at 4° C. The upper aqueous phase of each sample was transferred to another new EP tube, to which isopropanol with a volume equal to the transferred upper aqueous phase was added and uniformly mixed with the transferred upper aqueous phase. The solution rested for 1 hour at −20° C., and then centrifuged at 12,000 g for 10 minutes at 4° C. The supernatant was discarded, and 1 mL of pre-cooled 75% ethanol was added to the RNA pellet and mixed by pipetting up and down. The solution was centrifuged at 12,000 g for 10 minutes at 4° C., and then the supernatant is discarded. The EP tube containing the RNA pellet was placed on a super-clean bench for 30 minutes to completely evaporate the ethanol, and the resultant was resuspended in 10 µL of DEPC-treated water to form a total RNA solution for the following reverse transcription. The concentration of the solution was measured by an ultraviolet spectrophotometer.

2) Reverse Transcription of RNA

For performing the reverse transcription, a solution with a total volume of 20 µl was prepared by mixing 2 µg of the extracted RNA, 0.5 µg of random primers, 4 µL of 5× Master Mix, and DEPC-treated water taking all the rest volume. The solution was incubated at 37° C. for 60 minutes to have the reverse transcription reaction to obtain cDNA, then inactivated at 80° C. for 15 seconds, and then stored at −20° C. for later use.

3) Real-Time Quantitative PCR (RT-PCR)

RT-PCR was performed by using the RNA reverse transcription kit and the SYBR fluorescent dye. A system with a total volume of 10 µL was prepared by mixing 1 µL of the obtained cDNA, 5 µL of 2×SYBP® Premix Ex Taq™ II, 0.5 µL of a mixture of forward primer and backward primer (10 µM), and sterilized water taking all the rest volume. The RT-PCR was performed according to instructions of the kit with a protocol as follows: unwinding at 95° C. for 10 minutes; performing PCR for 40 cycles, each of which was performed by sequentially subjecting the system at 95° C. for 30 seconds, at 55° C. for 30 seconds, and at 72° C. for 20 seconds; and finally observing and analyzing a dissociation curve performed by sequentially subjecting the system at 95° C. for 15 seconds, at 60° C. for 15 seconds, and at 95° C. for 15 seconds). β-actin was used as an internal reference, the primer sequences used in the experiment were as follows:

```
PCR primers for IL-6:
                                (SEQ ID NO: 1)
Forward primer: 5'-TTTTGTACTCATCTGCACAGC-3'

(SEQ ID NO: 2)
Backward primer: 5'-GGATTCAATGAGGAGACTTGC-3'

PCR primers for β-actin:
                                (SEQ ID NO: 4)
Forward primer: 5'-ATCATGTTTGAGACCTTCAA-3'

(SEQ ID NO: 5)
Backward primer: 5'-AGATGGGCACAGTGTGGGT-3'
```

(2) Protein Detection

The HAECs that were previously cultured in a 6-well cell culture plate were divided into 3 different experimental groups, the control (Ctrl) group, the PA group, and the DAP+PA group. The cells of the DAP+PA group were applied with daphnetin in a concentration of 100 µM followed with a 24-hour incubation. Then, the cells of both the PA group and the DAP+PA group were applied with 500 µM palmitic acid, all followed with another 24-hour incubation. The protein detection was respectively carried out on each group of cells as follows.

1) Protein Extraction

The medium for cell culture in the wells was removed. 150 µL of IP lysis buffer was added to each well of the culture plate. The cultured cells in the wells were scraped by using a cell scraper, collected and transferred to a 1.5 mL EP tube, and subjected to vibrating for 15 seconds and cooling in ice bath for 10 minutes. The vibrating and cooling were repeated three times, ensuring that the cells were ice bathed for at least 30 minutes. Then, the samples were centrifuged at 12,000 g for 10 minutes at 4° C. The supernatants were collected, and the proteins therein were quantified by bicinchoninic acid (BCA) assay, and normalized. Then, the supernatants were added with 5× loading buffer and mercaptoethanol, and boiled for 10 minutes to denature the proteins. The extracted proteins were stored at −80° C. for later use.

2) Western Blot

10 µg of the extracted proteins were subjected to gel electrophoresis with 10% acrylamide gel, and electrophoretic transferred onto a PVDF membrane, which were blocked, and incubated with a primary antibody at 4° C. overnight, free primary antibody was washed away. Then, the membrane was incubated with a secondary antibody at room temperature for 1 hour, and free secondary antibody was washed away. Target proteins were detected by chemiluminescence.

4. Statistical Analysis

Figure 2:
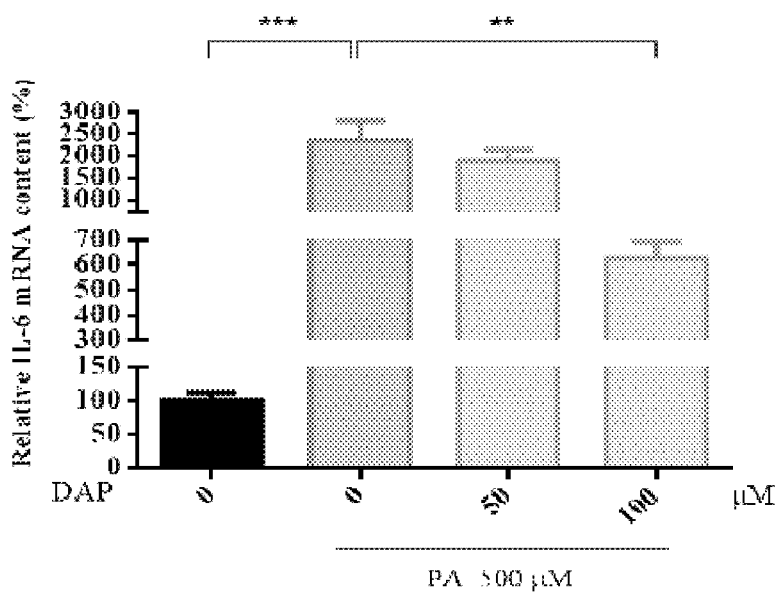
FIG. 2 is a diagram showing the inhibitory effect of an embodiment of daphnetin in different concentrations on palmitic acid-induced inflammation of human aortic endothelial cells, wherein the abscissa represents the concentration of daphnetin (DAP), and the ordinate represents mRNA level corresponding to IL-6.
Figure 3A:
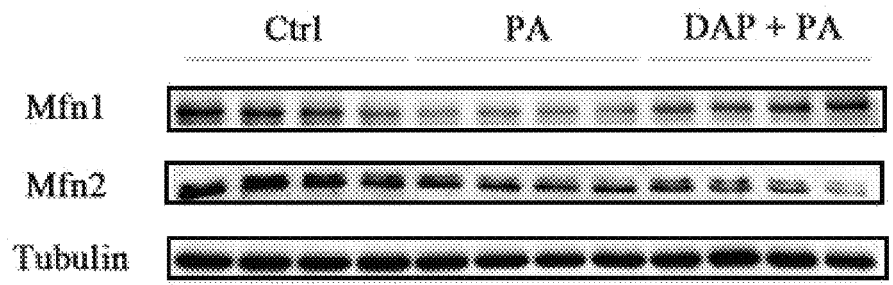
Figure 3B:
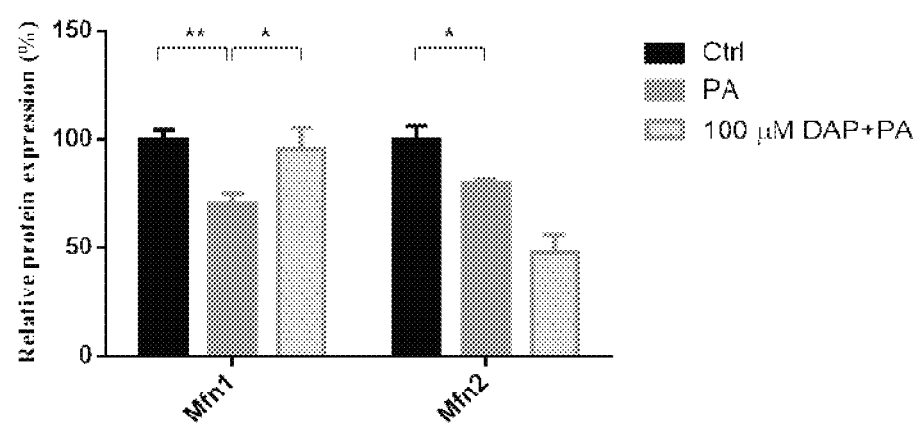

Referring to FIG. 1, FIG. 2, and FIG. 3B, the data obtained in the above-described experiments were expressed in the diagrams in form of mean±SEM (SEM is standard error of mean), and the data were analyzed by using One-way ANOVA analysis method with statistical significance p values of * meaning $p<0.05$,  meaning $p<0.01$, * meaning $p<0.001$.

5. Viability Increase of HAECs Inhibited by Saturated Fatty Acid

Referring to FIG. 1, the left set of data (in black) corresponds to the cells that were not treated with palmitic acid, and the right set of data (in grey) corresponds to the cells that were treated with palmitic acid. It can be seen from the right set of date that the palmitic acid treated cells which were previously treated with daphnetin in the concentration of 10 µM show higher viabilities than the palmitic acid treated cells without the daphnetin treatment, revealing that daphnetin is capable of increasing the viability of the palmitic acid inhibited cells.

6. Inhibitory Effect of Daphnetin on Palmitic Acid-Induced Inflammation of HAECs Daphnetin is capable of significantly inhibiting the inflammatory response caused by palmitic acid induced damage to the human vascular endothelial cells. Referring to FIG. 2, from left to right along the abscissa, the first data (in black) corresponds to the cells of the control group, the second data (in darker grey) corresponds to the cells that were treated with palmitic acid without the daphnetin treatment, the third and fourth data (in lighter grey) corresponds to the cells that were previously treated with daphnetin in different concentrations and then treated with palmitic acid. 500 µM of palmitic acid induced an inflammatory response in human aortic endothelial cells. As shown in FIG. 2, the cellular inflammatory factor, interleukin (IL-6), was significantly higher in palmitic acid treated cells than that in the control group. The mRNA level corresponding to IL-6 was increased for about 20 times, revealing that the level of inflammation in the 500 µM palmitic acid treatment group, was increased significantly. It can be seen from FIG. 2 that by applying daphnetin with the concentration of 100 µM, the mRNA level corresponding to IL-6 was significantly decreased, revealing a significant inhibition of the inflammatory response. The inhibition effect increases with the concentration of daphnetin. Daphnetin was thereby indicated to have an anti-inflammation effect and an anti-atherosclerosis effect.

7. Up-Regulating Effect of Daphnetin on a Palmitic Acid-Induced Decrease of Expression of Mitochondrial Membrane Fusion Related Protein Mfn1 in Human Aortic Endothelial Cells Mitochondrial fusion and division can not only change the morphology of mitochondria, affect the function of mitochondria, but also affect the survival of cells. Mitochondrial division and fusion are precisely regulated by a variety of proteins. The proteins involved in mitochondrial fusion mainly include Mfn1, Mfn2, and OPA 1. FIG. 3A and FIG. 3B show that palmitic acid is capable of reducing the expression of mitochondrial membrane fusion related proteins Mfn1 and Mfn2 in human aortic endothelial cells, while daphnetin is capable of significantly increasing the expression of Mfn1, thereby promoting cell fusion and maintaining mitochondrial homeostasis.

The above experimental results demonstrate that daphnetin is capable of promoting the growth of human aortic endothelial cells inhibited by saturated fatty acids, and effectively inhibiting the inflammatory response and mitochondrial damage of human aortic endothelial cells induced by high fat, thereby improving the function of human aortic endothelial cells.

Daphnetin can be used in preparing a pharmaceutical composition, such as a medicine or a drug, for improving aortic endothelial cell function.

In some embodiments, the pharmaceutical composition promotes the growth of human aortic endothelial cells inhibited by saturated fatty acids, and inhibits the inflammatory response of aortic endothelial cells caused by saturated fatty acids.

In some embodiments, the pharmaceutical composition reduces the mRNA level of IL-6 in aortic endothelial cells.

In some embodiments, the pharmaceutical composition protects mitochondria from being damaged by inflammation of aortic endothelial cells caused by a saturated fatty acid.

In some embodiments, the pharmaceutical composition increases the expression of mitochondrial membrane fusion related protein Mfn1.

A dysfunction of endothelial cell is the initial characterization, the reason, and the basis of occurrence and development of atherosclerosis which is a chronic inflammatory response. The occurrence of the inflammatory response is an important cause of atherosclerosis. Meanwhile, it is reported that a damage of the mitochondria may also be one important cause of atherosclerosis since the damage may induce an energy deficiency and function deterioration of endothelial cells. Daphnetin provided in the present disclosure exhibits excellent properties in protecting endothelial cells from inflammation and protecting mitochondria from being damaged in the endothelial cell damage test. Therefore, the composition provided in the present disclosure has a good prospect in prevention of cardiovascular diseases, such as atherosclerosis, that has an endothelial damage caused by high fat. Daphnetin provides a new medical approach for treatment of cardiovascular diseases caused by imbalance of dietary.

In some embodiments, daphnetin provided in the present disclosure can be used in preparing a medicine or a nutritional supplement for prevention or treatment of cardiovascular diseases.

In some embodiments, daphnetin provided in the present disclosure can be used in preparing a medicine or a nutritional supplement for prevention or treatment of atherosclerosis.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A method for improving function of an aortic endothelial cell, the method comprising contacting the cell with an effective amount of daphnetin.

2. The method for claim 1, wherein the daphnetin inhibits saturated fatty acid induced inflammation of an aortic endothelial cell.

3. The method for claim 1, wherein the daphnetin reduces a mRNA level corresponding to interleukin-6 in an aortic endothelial cell.

4. The method for claim 1, wherein the daphnetin protects a mitochondrion from being damaged by saturated fatty acid induced inflammation of an aortic endothelial cell.

5. The method for claim 1, wherein the daphnetin increases an expression of mitochondrial complex I protein in an aortic endothelial cell.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Forward primer for IL-6

<400> SEQUENCE: 1
ttttgtactc atctgcacag c                                              21

<210> SEQ ID NO 2
<211> LENGTH: 21
<212> TYPE: DNA
<213> ORGANISM: Artificial Sequence
<220> FEATURE:
<223> OTHER INFORMATION: Backward primer for IL-6

<400> SEQUENCE: 2
```

```
ggattcaatg aggagacttg c                                              21

<210> SEQ ID NO 3
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 3
atcatgtttg agaccttcaa                                                20

<210> SEQ ID NO 4
<211> LENGTH: 19
<212> TYPE: DNA
<213> ORGANISM: Artificial Sequence
<220> FEATURE:
<223> OTHER INFORMATION: Backward primer for beta-actin

<400> SEQUENCE: 4
agatgggcac agtgtgggt                                                 19
```